United States Patent [19]

Hough et al.

[11] Patent Number: 5,165,078
[45] Date of Patent: Nov. 17, 1992

[54] MULTI-CHANNEL, MULTI-WAVELENGTH DETECTION SYSTEM

[75] Inventors: David L. Hough, Edwardsburg, Mich.; Willis E. Howard, III, Elkhart, Ind.; Donald L. Jaworski, South Bend, Ind.

[73] Assignee: Miles Inc., Elkhart, Ind.

[21] Appl. No.: 674,458

[22] Filed: Mar. 25, 1991

[51] Int. Cl.⁵ .............................................. G02B 26/02
[52] U.S. Cl. .................................. 359/233; 359/889; 359/821; 250/232
[58] Field of Search .............. 359/210, 233, 234, 235, 359/236, 885, 889, 821; 250/232, 233

[56] References Cited

U.S. PATENT DOCUMENTS

| | | | |
|---|---|---|---|
| 2,265,149 | 12/1941 | Crane et al. | 359/233 |
| 3,333,505 | 8/1967 | Unuma | 359/889 |
| 4,165,919 | 8/1979 | Little | 359/234 |

Primary Examiner—Loha Ben
Attorney, Agent, or Firm—Roger N. Coe

[57] ABSTRACT

A radiation aperture system where two sets of apertures are distributed in ring sections of like radius on two parallel rings. As one ring is rotated with respect to its counterpart, one aperture of each ring will align to pass a radiation beam through both apertures. Only a single aperture pair is formed at each unique time, allowing sequential measurements of all combinations of both aperture openings during rotation without halting the rotation.

8 Claims, 2 Drawing Sheets

MULTI-CHANNEL, MULTI-WAVELENGTH DETECTION SYSTEM

BACKGROUND

1. The Field of the Invention

The present invention relates to a method of transmitting radiation, such as light, through a group of apertures. More specifically, the present invention is directed towards two parallel rings of radiation apertures, one ring being mounted on a rotatable base. As the rotatable ring is rotated, only one aperture of one ring at most will align at any unique time with an aperture in the other ring, in order to pass a beam of light through both apertures.

2. The Prior Art

Parallel rings of apertures are well known in the art, usually with one set of apertures being filters and the other set of apertures being detectors. In the prior art, however, both sets generally have equal numbers of apertures equally spaced around the rings. This means that when one pair of apertures aligns to pass a beam of light, all of the pairs of apertures align to pass beams of light.

One variation of this method increases the number of apertures in one of the rings by an integral amount. For example, one system may double the number of apertures in the second ring. This means that when any one pair of apertures aligns, one half of the apertures of the second ring also align.

Another type of ring aperture system aligns only one aperture pair at any unique time. In these systems, however, one of the rings consists of only a single aperture.

The third type of ring aperture system uses a plurality of apertures in both of the rings, and still aligns only one aperture pair at any unique time. This system groups all of the apertures of one ring into a portion of a circle, the arc of the circle being smaller than the arc of the distance between the apertures of the counterpart ring. Thus, if one plurality contained four apertures equally spaced around the ring, then the counterpart ring would have all of its apertures located within a distance of less than one quarter of its arc.

BRIEF SUMMARY AND OBJECTS OF THE INVENTION

The present invention is directed towards a system of radiation apertures arranged in two parallel rings.

An object of the present invention is to provide a ring aperture system wherein, when one ring is rotated with respect to its counterpart, only one aperture pair is aligned at any unique time during a single rotation. Further, the circle or portion of the circle of apertures of one ring is larger in arc than the arc between the apertures of its counterpart.

Another object of the present invention is to provide a ring aperture system wherein light scattered from one aperture is blocked from entering the aligned aperture counterpart.

Yet another object of the present invention is to provide a ring aperture system wherein one plurality of apertures are radiation filters.

Yet another object of the present invention is to provide a ring aperture system wherein one plurality of apertures are radiation detectors.

Still another object of the present invention is to provide a light filtering and detecting system for the spectrum between infrared and ultraviolet frequencies.

Yet another object of the present invention is to provide a light filtering and detecting system that may be used to filter and detect light emitted or reflected from a sample of a material to be tested by the emitted or reflected light.

Ring apertures systems may generally be divided into three types. In the first type, all of the apertures of at least one ring align with a counterpart at the same time. With the second type of system, one ring consists of only a single aperture. In the third type of ring system, the apertures of one ring are grouped into a portion of a circle. The arc of that portion is less than the arc between apertures of the counterpart ring. This third type of system is very inefficient, wasting a large part of the rings circumference.

The present invention is comprised of two parallel rings or portions of rings of apertures. The apertures are positioned such that the arcs between apertures of one ring are different than the arc between apertures of the counterpart ring. Also, the portions of rings of one plurality of apertures have a greater arc than the arc between apertures of the counterpart plurality of apertures. More specifically, when one ring is rotated with respect to the other, no more than one pair of apertures align at any unique time during a single rotation. This allows both rings to use a large portion, if not all, of their circumference.

A specific use for the present invention is in material testing devices. Generally in these devices, a small sample of the material to be tested is illuminated with radiation, typically from the infrared, visible light, or ultraviolet spectrum. The frequencies of light reflected or emitted from the sample are detected and analyzed, providing information on the nature of the material.

One advantage of the present invention occurs when one plurality of apertures are radiation detectors for detecting radiation beams passed through the other plurality of apertures. The present invention allows the beams emitted from the sample to be detected at a much faster rate than other prior art systems using similar detection systems.

Therefore, in one respect, the present invention relates to radiation aperture system comprising:

a first plurality of aperture means, positioned so as to form at least a portion of a circular ring about a center, a second plurality of aperture means, positioned such that i) the aperture means form at least a portion of a second circular ring about a center, the radius of the second circular ring being equal to the radius of a first circular ring, ii) the plane of the second circular ring is substantially parallel to the plane of the first circular ring, iii) the center of the second circular ring is substantially aligned with the center of the first circular ring along a line substantially perpendicular to the planes of both rings, iv) when the second circular ring is rotated about its center, the center of no more than one aperture means of the first plurality will, at any unique time, substantially align with the center of any of the aperture means of the second plurality, along a line substantially perpendicular to the planes of both rings, and a rotatable rotating means for rotating the second circular ring about its center in a plane substantially parallel to the plane of the first circular ring.

In another aspect of the invention, one or more of the aperture means is elevated away from the plane of the ring, the plane of the elevated aperture means being substantially parallel to the plane of the ring.

At least one plurality of apertures of the radiation aperture system may be filters. Also, at least one plurality of apertures of the radiation aperture system may be radiation detectors. Additionally, at least one plurality of apertures of the radiation aperture system may be entrances to radiation guide means. Yet another radiation aperture system may have at least one plurality of apertures wherein the apertures are lenses.

The present invention may further comprise blocking means for blocking radiation scattered from apertures of the first plurality to apertures of the second plurality, the blocking means being interposed between the first plurality of apertures and the second plurality of apertures.

Again, this has an advantage when one plurality of apertures are detectors designed to sample radiation beams passed through the other plurality of apertures. The blocking means reduces the number of erroneous signals picked up by the detectors.

Specifically, the radiation aperture system may further comprise radiation guide means, running a majority of the distance between the rings, a guide means encircling each aperture of at least one of the pluralities of apertures. Also, the radiation aperture system means may still further comprise a narrowing means within the guide means for narrowing the width of the radiation guide means such that the illumination of the walls of the guide means on the exit side of the narrowing means is reduced.

Moreover, the radiation aperture system may yet still further comprise a blocking radiation means wherein the entrance of the narrowing means is wider than the exit of the narrowing means. Also, the surface of the radiation guide exposed to radiation may be unreflective.

APERTURE ANGLE SELECTION

One preferred method of determining the arc between apertures of each aperture ring requires knowing in advance the number of desired first ring apertures ($N_1$). If equidistant apertures are desired for the first ring, then the arc between the apertures is an angle $$(\alpha) = \frac{360°}{N_1}.$$

If a larger gap is desired between the first and last apertures on the first ring, then $$\alpha < \frac{360°}{N_1}.$$

Next, the angular difference ($\delta$) between apertures of the first and second rings is selected. In the preferred embodiment, stepping motors drive the rotation of the moving ring. If stepping motors are used, then $\delta$ should be equal to the arc of an integral number of half steps of the stepping motor.

The number of second ring apertures (N2) is chosen next. There are two potential angles ($\beta a$ and $\beta b$) for the arc between the second ring apertures, were $\beta a = \alpha + \delta$ and $\beta b = \alpha - \delta$. If $\beta a \times N2 \leq 360°$, then the arc between the filters should have an angle of $\beta a$. If $\beta b \times N2 \leq 360°$, then the arc between the filters should have an angle of $\beta b$. Otherwise, the number of first ring apertures (N1), the number of second ring apertures (N2), and the angular difference ($\delta$) between the two are incompatible, and a new set of parameters must be chosen.

DETAILED DESCRIPTION OF THE PREFERRED EMBODIMENTS

Reference is now made to the drawings wherein like parts are designated with like numerals throughout.

Figure 1:
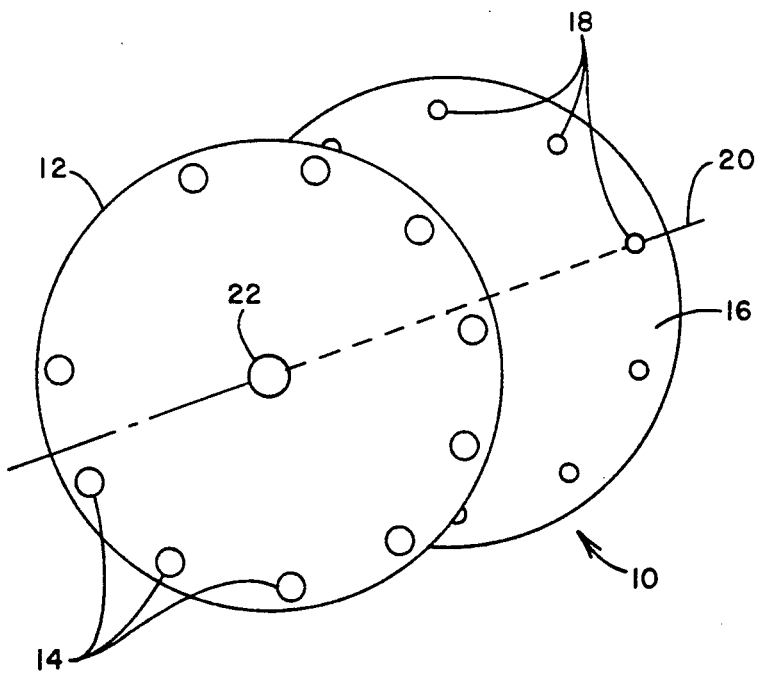
FIG. 1 shows an elevated angled view of one embodiment of the present invention.

FIG. 1 illustrates a filter/detector ring system (10) according to the present invention. A ring (12) contains the first plurality of radiation apertures in the form of monochromatic light filters (14). In this particular embodiment, the filters (14) are monochromatic light filters operating at frequencies between the infrared and ultraviolet range. Other embodiments, however, should not be restricted to these limitations.

A second ring (16) contains the second plurality of radiation apertures in the form of light detectors. Again, the detectors of this embodiment are primarily for frequencies around the visible light spectrum, but other embodiments should not be limited by this embodiment. The rings are substantially parallel, their centers lying on an axis (20) perpendicular to the planes of both of the rings. A rotatable rotating means (22) is capable of rotating the first ring (12) about its center axis (20).

Figure 2:
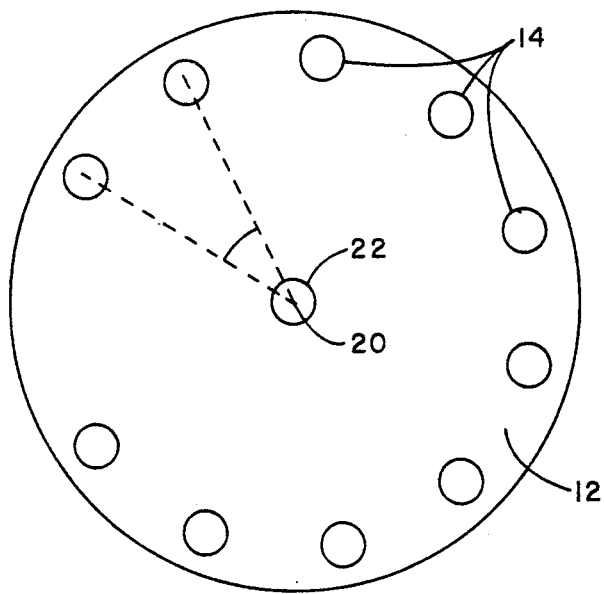
FIG. 2 illustrates a front view of a filter ring within the scope of the present invention.

FIG. 2 illustrates the filter ring (12) in greater detail. Ten monochromatic light filters (14) are arranged around the ring (12) so as to form a portion of a ring. The filters (14) are spaced at an arc of 32.4 degrees apart, leaving a gap of 68.4 degrees between two of the filters.

Figure 3:
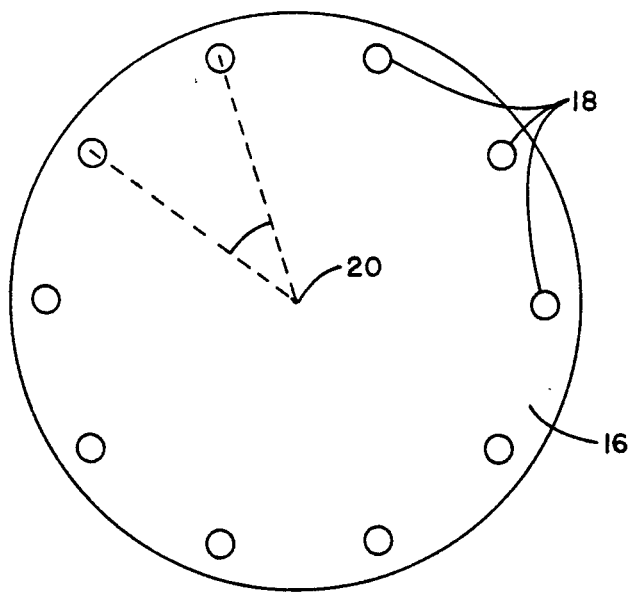
FIG. 3 shows a front view of a detector ring according to one embodiment of the present invention.

FIG. 3 shows a more detailed view of the detector ring (16). The detector ring (16) contains ten light detectors (18), arranged to form a ring about the ring. The detectors (18) are spaced equidistantly around the ring at an arc distance of 36 degrees.

The portion of the ring of filters (14) and the ring of detectors (18) share the same radius from their centers, which lie along the same axis (20).

In preparing this embodiment of the present invention for operation, the light beams to be detected are directed to the detectors at an angle perpendicular to the plane of the detectors, and so as to pass through the plane of the filters. More particularly in this embodiment, ten individual light beams are directed towards each of the light detectors (18) through the plane of the filter ring. This may be done using fiber optic light guides, positioned almost flush with the filter ring.

In operating this embodiment of the present invention, and referring back to FIG. 1, the rotating means (22), preferably a stepping motor, rotates the filter ring (12) about its center axis (20). As the filter ring (12)

rotates, the centers of each of the individual filters (14) will, at unique times for each individual filter/detector combination, align with the centers of each of the detectors (18) along lines perpendicular to the planes of the filter ring and detector ring. Since each of these lines coincides with a light beam to be detected, each light beam is passed through a filter to a detector when they align. During one rotation of the filter ring, each of the ten light beams will be filtered by each of the ten filters (14) only once, and at unique times. Since the position of the rotating ring may be determined from the stepping motor, the detectors (18) need only be activated when a given filter aligns with a detector.

Figure 4:
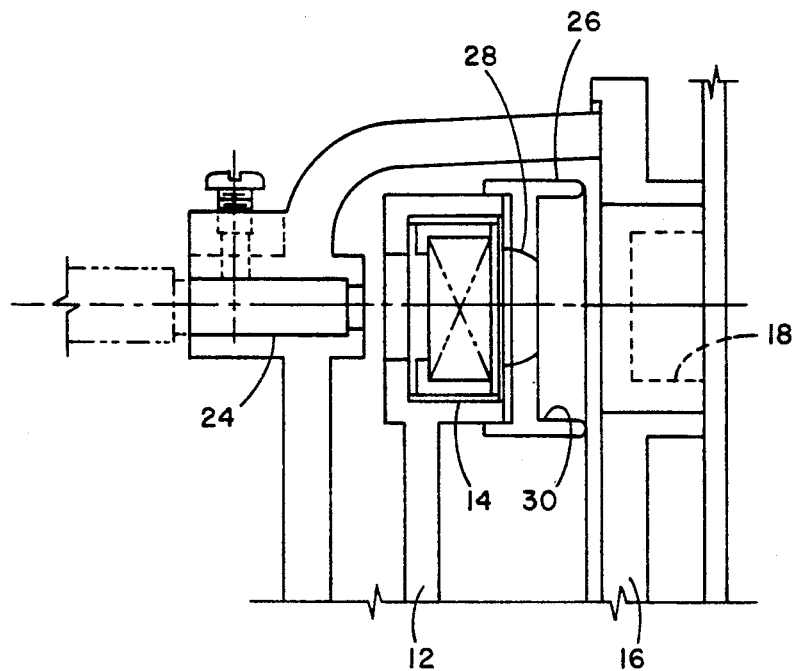
FIG 4 illustrates an elevated side view of one embodiment of a blocking device within the scope of the invention.

Referring now to FIG. 4, one embodiment of the blocking means of the present invention is illustrated. The described embodiment is directed towards blocking the scattering of light beams.

The light beam to be filtered is guided to the filter/detector ring system by filter optic light guides (24). When the filter (14) is aligned with a light beam, the light beam passes through the filter (14) on to the blocking means (26).

The walls (28) of the narrow portion of the blocking means (26) are slanted inward, towards the radiation detector (18). Thus, if part of the light beam is scattered off of these walls, the scattered light will be directed away from the aperture of the radiation detector (18).

Also, the walls (30) of the wide portion of the blocking means (26) are located away from the narrow walls (28). This is done such that light passing through the narrow portion will not be scattered off of the walls (30) of the wider portion and into the detector (18).

Further variations and modifications of the foregoing will become apparent to those skilled in the art and are intended to be encompassed by the claims appended hereto.

We claim:

1. A radiation aperture system comprising:
   a first plurality of nonmovable aperture means, positioned so as to form at least a portion of a first circular ring about a first center;
   a second plurality of aperture means, positioned such that
   (i) said second plurality of aperture means form at least a portion of a second circular ring about a second center, the radius of said second circular ring being equal to the radius of said first circular ring,
   (ii) the plane of said second circular ring is substantially parallel to the plane of said first circular ring,
   (iii) the second center is substantially aligned with the first center along a line substantially perpendicular to said planes of both rings,
   (iv) when said second circular ring is rotated about the second center, no more than one aperture means of said first plurality will, at any unique time, substantially align with any of said aperture means of said second plurality along a line substantial perpendicular to said planes of both rings;
   a rotatable rotating means for rotating said second circular ring about the second center in a plane substantially parallel to said plane of said first circular ring; and
   wherein the first and second plurality of aperture means have different arcs between their respective aperture means.

2. A radiation aperture system according to claim 1 wherein at least one of said aperture means is elevated away from said plane of its corresponding circular ring, the plane of said elevated aperture means being substantially parallel to the plane of said circular ring.

3. A radiation aperture system according to claim 1 wherein the aperture means of said first plurality and said second plurality align only once for each rotation of said second circular ring.

4. A radiation aperture system according to claim 1 further comprising a blocking means for blocking scattered beams of radiation from being transmitted through the radiation aperture system, said blocking means being interposed between said first plurality of aperture means and said second plurality of aperture means.

5. A radiation aperture system according to claim 4 wherein said blocking means further comprises radiation guide means running a majority of the distance between said first circular ring and said second circular ring.

6. A radiation aperture system according to claim 1 wherein at least one plurality of aperture means is comprised of radiation filters.

7. A radiation aperture system according to claim 1 wherein at least one plurality of aperture means is comprised of radiation detectors.

8. A radiation aperture system according to claim 1 wherein at least one plurality of aperture means is comprised of lenses.

* * * * *